United States Patent [19]

Meffert Alfred et al.

[11] 4,324,740

[45] Apr. 13, 1982

[54] PREPARATION OF 2-PHENYLETHYLENE PHOSPHONIC ACID

[75] Inventors: Meffert Alfred; Holger Tesmann, both of Düsseldorf, Fed. Rep. of Germany

[73] Assignee: Henkel Kommanditgesellschaft auf Aktien, Düsseldorf-Holthausen, Fed. Rep. of Germany

[21] Appl. No.: 240,394

[22] Filed: Mar. 4, 1981

[30] Foreign Application Priority Data

Mar. 19, 1980 [DE] Fed. Rep. of Germany ....... 3010471

[51] Int. Cl.³ .............................................. C07F 9/38
[52] U.S. Cl. ............................................. 260/502.4 R
[58] Field of Search ................................. 260/502.4 R

[56] References Cited

U.S. PATENT DOCUMENTS 2,685,602  8/1954  Woodstock et al. ........ 260/502.4 R
3,763,122  10/1973  Effers ................................ 526/278
3,931,294  1/1976  Auel et al. ................... 260/502.4 R

FOREIGN PATENT DOCUMENTS 76974  11/1970  German Democratic Rep. ............................. 260/502.4 R

OTHER PUBLICATIONS

Kosolapoff et al., "J. Am. Chem. Soc.," vol. 68, (12/1946), pp. 2540-2541.
Pudovik et al., "Russian Chemical Reviews", 37(5) 1968, pp. 317-332.

Primary Examiner—Joseph E. Evans
Attorney, Agent, or Firm—Hammond & Littell, Weissenberger and Muserlian

[57] ABSTRACT

This invention is directed to an improved process for preparing 2-phenylethylene phosphonic acid by reacting styrene and $PCl_5$ in an inert organic solvent and hydrolyzing the reaction product formed, wherein the improvement comprises forming a mixture of styrene and $PCl_5$ in a molar ratio of about 1:1 at a temperature of from 60° to 70° C. in an inert organic solvent having a boiling point above 70° C.; maintaining the mixture at a temperature of from 60° to 70° C. with evolution of HCl gas until a clear solution forms; distilling off the solvent under vacuum; hydrolyzing the remaining reaction mixture in water at temperatures not exceeding 70° C. and cooling the hydrolyzed mixture to cause crystals of 2-phenylethylene phosphonic acid to precipitate; and recovering said crystals.

1 Claim, No Drawings

PREPARATION OF 2-PHENYLETHYLENE PHOSPHONIC ACID

FIELD OF THE INVENTION

This invention is directed to the preparation of 2-phenylethylene phosphonic acid. More specifically, this invention is directed on improved method of preparing 2-phenylethylene phosphonic acid by reacting styrene with $PCl_5$.

BACKGROUND OF THE INVENTION

The reaction with styrene with twice the molar amount of $PCl_5$ in the presence of an inert organic solvent such as benzene and the subsequent conversion into 2-phenylethylene phosphonic acid by hydrolysis is known. The pure acid is obtained with a total yield of approximately 34% subsequently to recrystallization from dibromomethane.

The preparation of 2-phenylethylene phosphonic acid by chlorination of a mixture of styrene and phosphorus trichloride and subsequent hydrolysis is also known. However, it is unavoidable during this reaction that a large amount of the added styrene escapes conversion into phosphonic acid due to the formation of chlorination products.

Finally, a continuous process has been disclosed in German Published Application (DE-OS) No. 23 43 460 in which 2-phenylethylene phosphonic acid is prepared by the reaction of styrene with twice the molar amount of $PCl_5$ and subsequent hydrolysis, $POCl_3$ being used as solvent. This process has the disadvantage that considerable amounts of $PCl_5$ as well as $POCl_3$ must be used.

OBJECTS OF THE INVENTION

It is an object of the invention to provide a method for the preparation of 2-phenylethylene phosphonic acid.

It is also an object of the invention to provide an improved method of preparing 2-phenylethylene phosphonic acid by reacting styrene and $PCl_5$ in an inert organic solvent and hydrolyzing the reaction product formed, wherein the improvement comprises forming a mixture of styrene and $PCl_5$ in a molar ratio of about 1:1 at a temperature of from 60° to 70° C. in an inert organic solvent having a boiling point above 70° C.; maintaining the mixture at a temperature of from 60° to 70° C. with evolution of HCl gas until a clear solutions forms; distilling off the solvent under vacuum; hydrolyzing the remaining reaction mixture in water at temperatures not exceeding 70° C. and cooling the hydrolyzed mixture to cause crystals of 2-phenylethylene phosphonic acid to precipitate; and recovering said crystals.

These and other objects of the invention will become more apparent from the discussion below.

DETAILED DESCRIPTION OF THE INVENTION

It has been found that the presently known process of preparing 2-phenylethylene phosphonic acid can be improved. According to the improved method, styrene and $PCl_5$ are mixed at a molar ratio of 1:1 and at temperatures of from about 60° to 70° C., in an inert organic solvent having a boiling point above 70° C., and the mixture is kept at this temperature under agitation with evolution of HCl gas until a clear solution is formed. The solvent is then removed under vacuum, the reaction product is transferred into water and hydrolyzed at a temperature not exceeding 70° C., and the product is crystallized from the subsequently cooled solution.

Suitable inert organic solvents for carrying out the process include, for example, benzene, toluene, chlorobenzene, xylene, and chlorinated hydrocarbons having a boiling point above 70° C. Advantageously the organic solvent is used in an amount such that from about 300 to 600 ml of solvent are available per mol of $PCl_5$.

When the stipulated conditions are observed, the process of the invention has the advantage that 2-phenylethylene phosphonic acid can be prepared with good yields and that only 1 mol of $PCl_5$ is needed per mol of styrene.

The 2-phenylethylene phosphonic acid can be used with good effect as a collector for the recovery of stannic oxide by flotation.

The following example is intended to illustrate the invention and is not to be construed as limiting the invention thereto.

EXAMPLE

Amounts of 18.5 kg of toluene and 20.8 kg of $PCl_5$ are placed in an enamelled agitator reactor and heated to 60° C. under agitation. At this temperature, 10.4 kg of styrene dissolved in 18.5 kg of toluene are added, the addition being controlled in such a manner that the exothermic reaction keeps the reaction temperature between 60° and 70° C. The agitation is continued at this temperature until an almost clear solution is obtained. The reaction time is approximately 4 to 5 hours. The HCl gas evolved during this time is removed through an absorption tower.

The toluene is then distilled off under vacuum, while the pot temperature is kept from rising above 70° C. The styryl phosphonic acid tetrachloride formed is transferred into 64 kg of water for the hydrolysis, while care is taken that the temperature does not exceed 70° C. 2-Phenylethylene phosphonic acid precipitates from the cooled hydrolysis mixture in the form of a white crystalline product. It is filtered off and dried at 70° C. The crude yield is 89 percent (based on styrene).

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. In a process for preparing 2-phenylethylene phosphonic acid by reacting styrene and $PCl_5$ in an inert organic solvent and hydrolyzing the reaction product formed, the improvement which comprises forming a mixture of styrene and $PCl_5$ in a molar ratio of about 1:1 at a temperature of from 60° to 70° C. in an inert organic solvent having a boiling point above 70° C.; maintaining the mixture under agitation at a temperature of from 60° to 70° C. with evolution of HCl gas until a clear solution forms; distilling off the solvent under vacuum; hydrolyzing the remaining reaction mixture in water at temperatures not exceeding 70° C. and cooling the hydrolyzed mixture to cause crystals of 2-phenylene phosphonic acid to precipitate; and recovering said crystals.

* * * * *

UNITED STATES PATENT AND TRADEMARK OFFICE
CERTIFICATE OF CORRECTION

PATENT NO. : 4,324,740
DATED : April 13, 1982
INVENTOR(S) : ALFRED MEFFERT et al.

It is certified that error appears in the above—identified patent and that said Letters Patent is hereby corrected as shown below:

Page 1, in the heading and in category [75], "Meffert Alfred" should read -- Alfred Meffert --.

Signed and Sealed this

Tenth Day of August 1982

SEAL]

*Attest:*

GERALD J. MOSSINGHOFF

*Attesting Officer*   *Commissioner of Patents and Trademarks*